(12) United States Patent
Bedor

(10) Patent No.: US 8,906,068 B1
(45) Date of Patent: Dec. 9, 2014

(54) SPINAL FIXATION SYSTEM AND METHOD

(76) Inventor: Bernard M. Bedor, Daytona Beach, FL (US)

( * ) Notice: Subject to any disclaimer, the term of this patent is extended or adjusted under 35 U.S.C. 154(b) by 264 days.

(21) Appl. No.: 13/231,042

(22) Filed: Sep. 13, 2011

(51) Int. Cl.
*A61B 17/70* (2006.01)

(52) U.S. Cl.
CPC .......... *A61B 17/7037* (2013.01); *A61B 17/7034* (2013.01)
USPC ............................. 606/267; 606/305; 606/272

(58) Field of Classification Search
CPC ........... A61B 17/7037; A61B 17/7034; A61B 17/704
USPC .......................................... 606/265–272, 305
See application file for complete search history.

(56) References Cited

U.S. PATENT DOCUMENTS

| | | | |
|---|---|---|---|
| 5,782,833 A | 7/1998 | Haider | |
| 6,280,442 B1 * | 8/2001 | Barker et al. | 606/60 |
| 6,471,705 B1 * | 10/2002 | Biedermann et al. | 606/271 |
| 6,843,791 B2 | 1/2005 | Serhan | |
| 7,144,396 B2 | 12/2006 | Shluzas | |
| 7,503,924 B2 | 3/2009 | Lee et al. | |
| 7,842,073 B2 | 11/2010 | Richelsoph et al. | |
| 7,879,075 B2 | 2/2011 | Shluzas | |
| 7,905,907 B2 | 3/2011 | Spitler et al. | |
| 7,922,748 B2 * | 4/2011 | Hoffman | 606/267 |
| 7,931,676 B2 * | 4/2011 | Veldman et al. | 606/261 |
| 7,942,909 B2 | 5/2011 | Hammill, Sr. et al. | |
| 7,947,065 B2 | 5/2011 | Hammill, Sr. et al. | |
| 2005/0080415 A1 | 4/2005 | Keyer et al. | |
| 2007/0270813 A1 * | 11/2007 | Garamszegi | 606/61 |
| 2008/0015584 A1 | 1/2008 | Richelsoph | |
| 2008/0045953 A1 * | 2/2008 | Garamszegi | 606/61 |
| 2008/0294202 A1 * | 11/2008 | Peterson et al. | 606/305 |
| 2009/0105756 A1 | 4/2009 | Richelsoph | |
| 2009/0192548 A1 | 7/2009 | Jeon et al. | |
| 2009/0204155 A1 * | 8/2009 | Aschmann | 606/264 |
| 2010/0094343 A1 | 4/2010 | Pham et al. | |

* cited by examiner

*Primary Examiner* — Ellen C Hammond
(74) *Attorney, Agent, or Firm* — Black, McCuskey, Souers & Arbaugh, LPA

(57) ABSTRACT

A spinal fixation system (1) for use in the fixation of a spine having a securing element (18) having a biasing member (21) located on a lower portion (44) of the securing element (18); and a substantially concave surface (25) dimensioned for at least partially circumscribing a fixation rod (15); and a retaining element (22) having: a substantially concave top surface (23) dimensioned for at least partially circumscribing a fixation rod (15); an outwardly extending wing (16); a crimping portion (42), wherein the crimping portion (42) at least partially compresses when a force is exerted on the retaining element (22); and a substantially concave bottom surface (24) dimensioned for at least partially circumscribing a head (11) of a bone fixation element (9).

8 Claims, 7 Drawing Sheets

SPINAL FIXATION SYSTEM AND METHOD

BACKGROUND OF THE INVENTION

1. Field of the Invention

The present invention relates to spinal fixation systems and methods, more specifically, a spinal fixation system that provides retention of a fixation rod wherein lateral and rotational movement of a fixation rod and bone fixation element are significantly reduced.

2. Description of Related Art

Spinal fixation, also referred to as vertebral fixation, is a neurosurgical procedure for reducing movement of a spine so as to decrease damage to the spinal cord and/or spinal roots. Spinal fixation is utilized to treat a wide variety of spinal disorders and deformities which result in vertebral displacement of the spine, including, but not limited to, scoliosis, kyphosis, spondylolisthesis, rotation, tumor diseases, disc degeneration, and congenital defects. In addition, spinal fixation is utilized to treat vertebral fractures, injuries, or other traumas to the spine wherein the spine becomes displaced from such fracture, injury, or trauma.

The procedure utilizes synthetic devices to anchor two or more vertebrae to one another in the spinal column. Such devices may include bone fixation elements, also referred to as bone screws, coupled to a spinal fixation rod via a coupling element. The bone fixation elements are inserted into the pedicle(s) of the desired vertebrae and are secured to or within the coupling element. The spinal fixation rod, in turn, is secured within the coupling element via a securing element. Accordingly, the spinal fixation rod is ultimately secured to the vertebrae such that movement of the stabilized vertebrae is limited. As the ultimate goal of spinal fixation is to limit movement of the spine, it is of great importance that fixation between the bone fixation element, coupling element, and fixation rod be rigid and permanent.

Various structures for securing the fixation rod within the coupling element are currently available. One such structure includes the use of a compression means, such as a compression screw, which exerts a predetermined amount of force on the fixation rod when the compression means is secured within the coupling element. Such compressive force also translates to a compressive force being applied on the coupling element and the bone fixation element as well, thereby reducing movement of the synthetic devices within the vertebra to which such synthetic devices are secured.

However, some synthetic devices require the bone fixation element to be secured within the coupling element at a substantially 90 degree angle thereto, thereby resulting in a substantially 90 degree insertion of the bone fixation element into the pedicle. Thus, use of such synthetic devices limits the ability to secure such devices at an angle customized to a patient, even if a more accurate and secure fixation would result if the bone fixation element were inserted into the pedicle at either an acute or obtuse angle. As such, there exists a need for an improved spinal fixation system that would permit rotational movement of a bone fixation element within the coupling element prior to insertion into a pedicle, but prevent movement thereof after insertion into the pedicle.

Moreover, although the compression means utilized in some synthetic devices results in a reduction of movement of the fixation rod within the coupling element, rotational movement of the fixation rod therein does not always result, as in some cases the compression means is not shaped so as to maximize the surface area contact between the compression means and the fixation rod. As such, there exists a need for an improved spinal fixation system that would limit both lateral and rotational movement of a fixation rod located within a coupling element.

Furthermore, some synthetic devices utilizing compression means may become loose over time due to vibrational forces applied thereto, thereby resulting in pain and discomfort in the patient and a need to perform corrective surgical procedures to re-tighten and re-secure the synthetic devices. As such, there exists a need for an improved spinal fixation system which would limit loosening of the synthetic devices due to vibrational forces.

SUMMARY OF THE INVENTION

The present invention is directed to a spinal fixation system having a biasing member located on a lower portion of the securing element; and a substantially concave surface dimensioned for at least partially circumscribing a fixation rod; and a retaining element having: a substantially concave top surface dimensioned for at least partially circumscribing a fixation rod; an outwardly extending wing; a crimping portion, wherein the crimping portion at least partially compresses when a force is exerted on the retaining element; and a substantially concave bottom surface dimensioned for at least partially circumscribing a head of a bone fixation element.

The present invention is also directed to a method for fixating a spine comprising positioning a bottom end of a coupling element having a pair of opposed longitudinal apertures through a wall thereof extending from a top end of the coupling element to an aperture bottom in spaced relation from the bottom end of the coupling element, the wall defining an interior space dimensioned for admitting a bone fixation element thereinto, the apertures dimensioned for admitting a fixation rod diametrically through the interior space; and a hole through the bottom end dimensioned for admitting a shank of the elongated bone fixation element therethrough and smaller than a head of the bone fixation element for retaining the head within the interior space, the shank extending downwardly from the bone fixation element adjacent to a bone in a spine; inserting a bone fixation element into the coupling element such that a shank of the bone fixation element is located within the interior space and the tip extends into the hole and is adjacent to the bone; driving the bone fixation element into the bone such that at least a portion of a shank of the bone fixation element extends through the hole and into the bone; inserting a retaining element dimensioned for insertion into the coupling element interior space atop the bone fixation element head, the retaining element for retaining the bone fixation rod within the interior space; admitting a fixation rod into a pair of opposed longitudinal apertures though a wall of the coupling element; inserting a securing element dimensioned for insertion into the coupling element interior space atop the fixation rod, such that a biasing member located on a lower portion of the securing element contacts the retaining element; mating a locking element with a mating element adjacent the top end of the coupling element, for retaining the fixation rod within the interior space; and securing the securing element within the coupling element to prevent rotation of the securing element about a longitudinal axis thereof.

DETAILED DESCRIPTION OF THE PREFERRED EMBODIMENTS

A description of the preferred embodiments of the present invention will now be presented.

Figure 1:
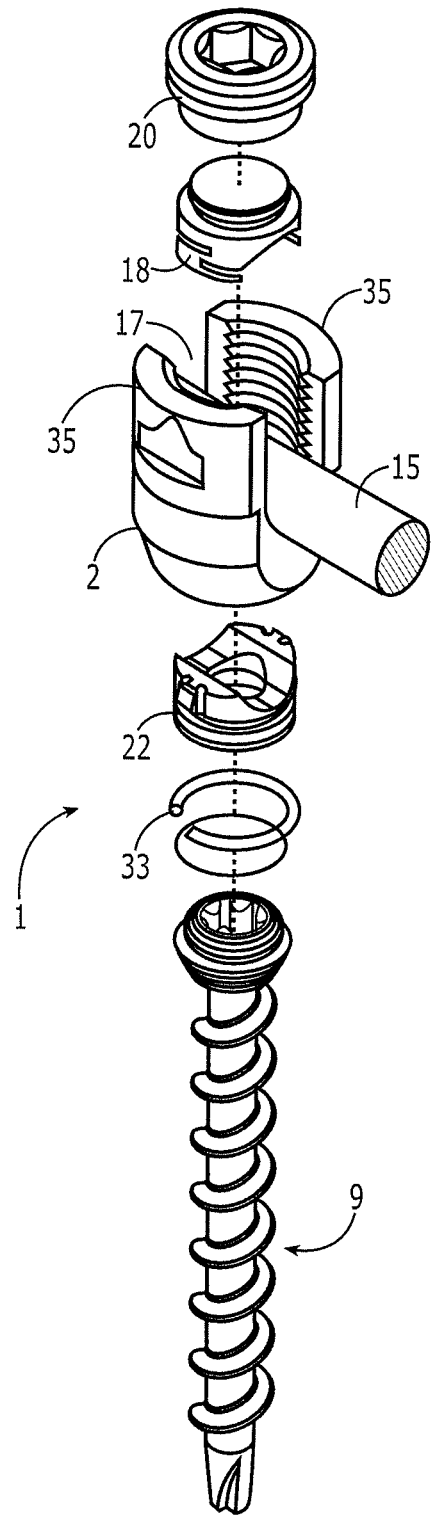
FIG. 1 is an isometric exploded view of a spinal fixation system.

With reference to FIG. 1, an isometric exploded view of a spinal fixation system is shown. The spinal fixation system 1 includes a coupling element 2 having walls 35 and at least one longitudinal aperture 17 and a securing element 18. When used in spinal fixation, a bone fixation element 9 and a fixation rod 15 are utilized. The spinal fixation system 1 may also include an optional locking element 20, a washer 28, and a retaining element 22.

Figure 2:
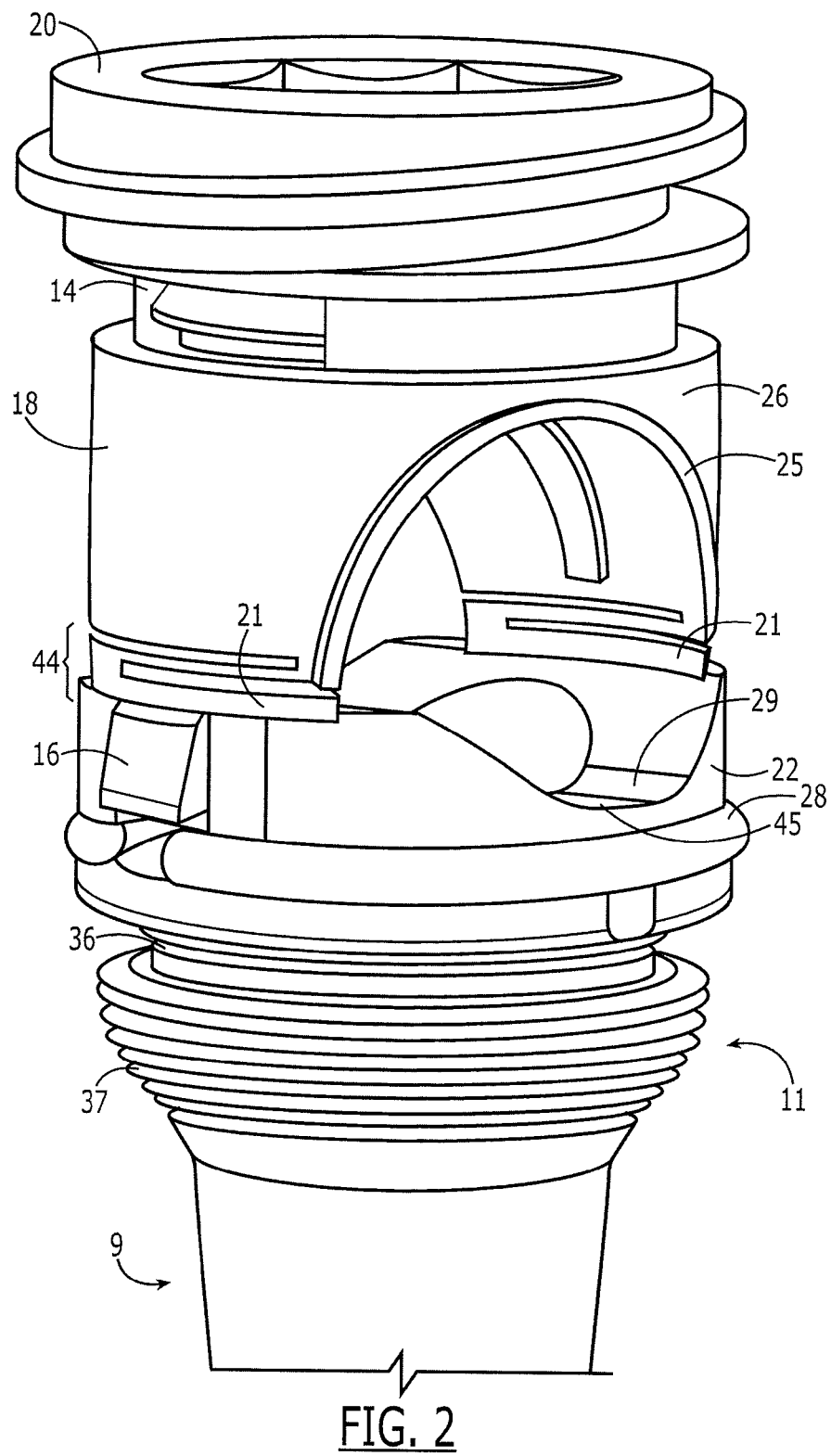
FIG. 2 is an enlarged view of a portion of a partially assembled spinal fixation system.

In FIG. 2, an enlarged view of a portion of a partially assembled spinal fixation system is shown. The securing element 18 includes a concave surface 25 which may include a raised portion 26 thereon. The securing element 18 may also include a biasing member 21 located on a lower portion 44 of the securing element 18. The biasing member 21 may be, but is not limited to, a spring.

An upwardly extending arm 14 may be located on the securing element 18 so as to be retained within the locking element 20. The bone fixation element 9 includes a head 11 having a first portion 36 and a second portion 37. The head 11, and, as shown, the first portion 36, may be secured within the retaining means 22. The retaining element 22 has a generally concave surface with contact areas 29. The contact areas 29 may extend in a linear increasing slope manner from a base section 45 toward an outwardly extending wing 16.

Figure 3:
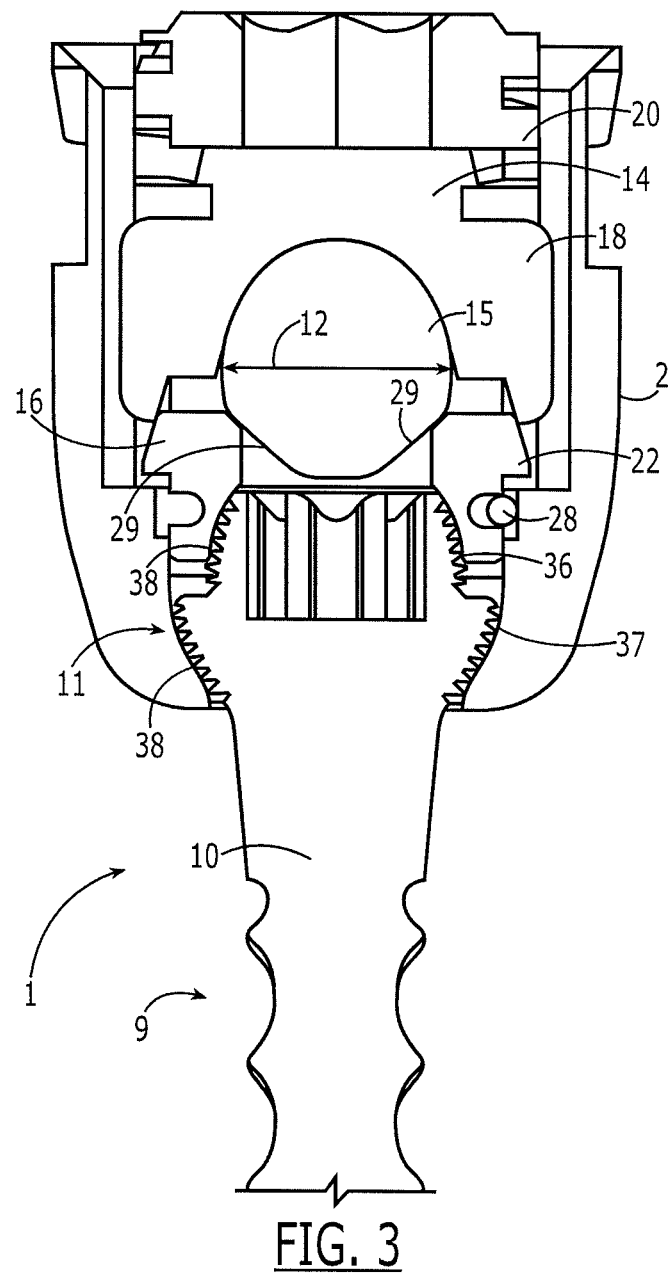
FIG. 3 is a cross sectional view of a spinal fixation system.

In FIG. 3, a cross sectional view of a spinal fixation system is shown. When assembled, the spinal fixation system 1 permits rigid fixation of the fixation rod 15 wherein a constant force is applied on the fixation rod 15 and rigid fixation of the bone fixation element 9 wherein a constant force is applied on the bone fixation element 9.

When assembled, the bone fixation element 9 is secured within the coupling element 2 such that a head 11 of the bone fixation element 9 is retained within the coupling element 2 while a shank 10 of the bone fixation element 9 extends through the coupling element 2. An optional washer 28 may be inserted into the coupling element 2 such that the washer 28 is located above the head 11 of the bone fixation element 9. A retaining element 22 is inserted into the coupling element 2 wherein the retaining element 22 is located atop the bone fixation element 9.

The head 11 of the bone fixation element 9 may include a first portion 36 and a second portion 37 wherein both the first portion 36 and second portion 37 include teeth 38 located thereon. The teeth 38 are uniform but asymmetrical, with each tooth having a moderate slope on one edge and a much steeper slope on the other edge. The first portion 36 and the second portion 37 may be different sizes. Although shown as concentric circles in circumference (as shown in greater detail in FIG. 15), the first portion 36 and the second portion 37 of the head 11 need not be concentric to one another. If the second portion 37 is greater in circumference than the first portion 36, greater support is provided on the coupling element 2.

The fixation rod 15, which has a rod diameter 12, is admitted through the longitudinal apertures 17 of the coupling element 2. The retaining element 22 is located between the fixation rod 15 and the head 11 of the bone fixation element 9. The securing element 18 is secured within the coupling element 2. If a locking element 20 is utilized, the securing element 18 is secured thereto and both are ultimately secured within the coupling element 2. To secure the securing element 18 to the locking element 20, an upwardly extending arm 14 may be utilized as described and depicted.

Figure 4:
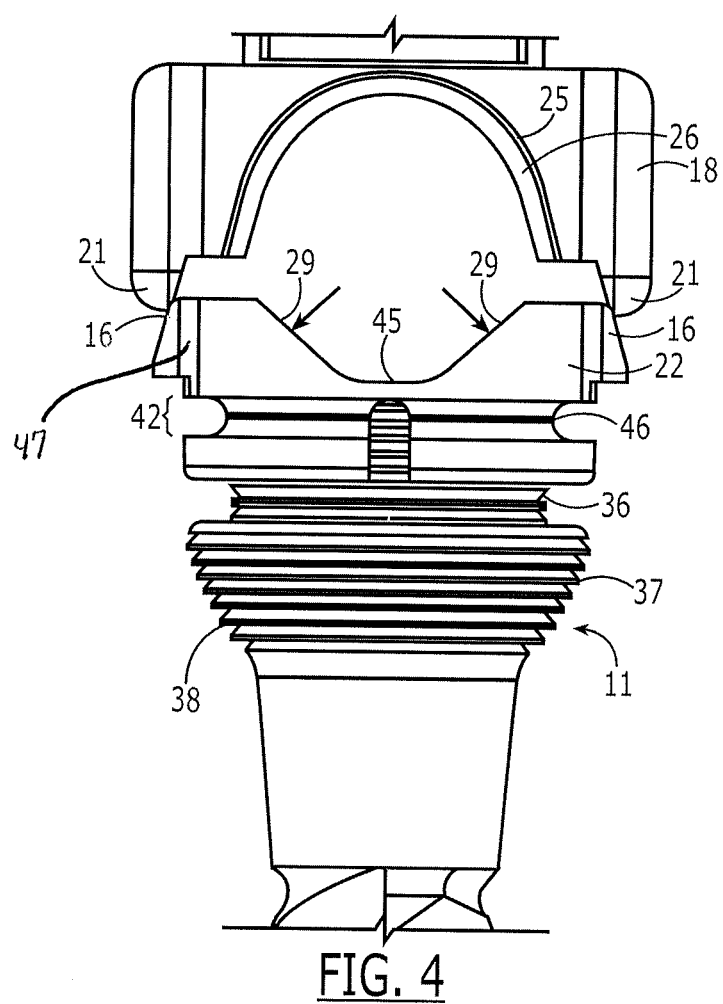
FIG. 4 is a side view of a partially assembled spinal fixation system.
Figure 5:
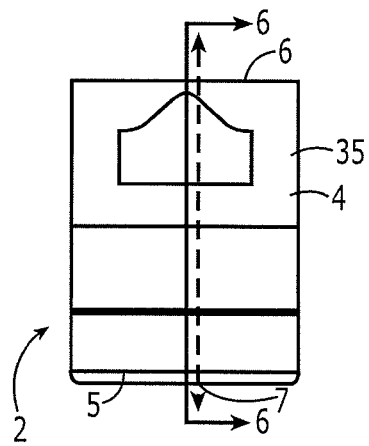
FIG. 5 is a side view of a coupling element of the spinal fixation system.
Figure 6:
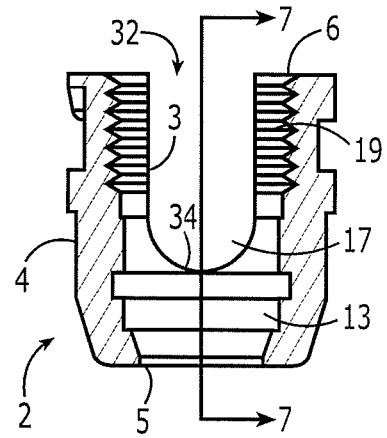
FIG. 6 is a cross-sectional view along lines 6-6 of the embodiment of FIG. 5.
Figure 7:
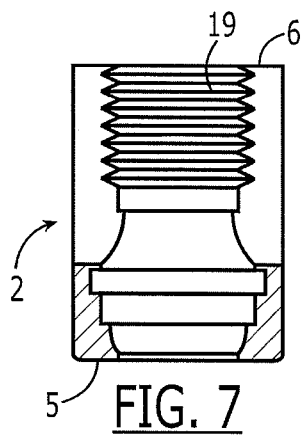
FIG. 7 is a cross-sectional view along lines 7-7 of the embodiment of FIG. 6.
Figure 8:
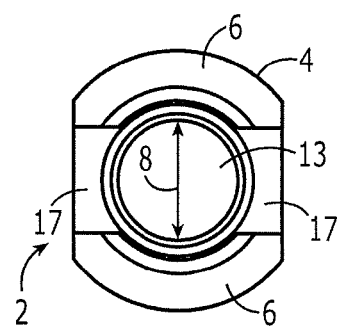
FIG. 8 is a top view of a coupling element of the spinal fixation system.
Figure 9:
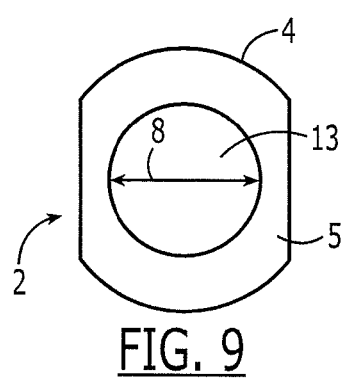
FIG. 9 is a bottom view of a coupling element of the spinal fixation system.

FIG. 4 shows a side view of a partially assembled spinal fixation system. The retaining element 22 may be formed so as to at least partially compress. As shown, the retaining element 22 includes slits 47 to permit such compression. However, other means for permitting such compression are envisioned. In one embodiment where the retaining element 22 may be compressed, the retaining element 22 holds the bone fixation element 9 and then compresses, at least partially, when the locking element 20 is tightened.

When the locking element 20 is tightened, a force is applied to the securing element 18. The force from the securing element 18 then translates force onto the retaining element 22. As the locking element 20 is tightened, the securing element 18 moves in a downward direction, first compressing the biasing members 21, then applying direct pressure on the fixation rod 15. The force applied on the fixation rod 15 translates force onto the contact area 29 of the retaining element 22. The force applied onto the contact area 29 causes the wings 16 to move outwardly, which in turn causes downward and inward movement of a portion of the retaining element 22. These forces work together to at least partially compress a crimping portion 42 of the retaining element 22, thereby grasping, crimping, or otherwise securing onto the head 11 of the bone fixation element 9.

FIGS. 5-9 show varying views of a coupling element of the spinal fixation system. The coupling element 2 has an exterior surface 4, a bottom end 5, a top end 6, and a longitudinal axis 7. The coupling element 2 also has a pair of opposed longitudinal apertures 17 through a wall 35 thereof extending from a top end 6 of the coupling element 2 to an aperture bottom 34 in spaced relation from a bottom end 5 of the coupling element 2. The apertures 17 may be substantially U-shaped as shown, but other shapes may also be utilized.

The wall 35 defines an interior space 32 dimensioned for admitting a bone fixation element 9 thereinto and the apertures 17 are dimensioned for admitting a fixation rod 15 diametrically through the interior space 32 of the coupling element 2. The coupling element 2 also includes a hole 13 through the bottom end 5 of the coupling element 2.

An optional mating element 19 may be located on an interior surface 3 of the coupling element 2. As shown, the mating element 19 may be threads; however, other mating elements may also be utilized.

The hole 2 has a diameter 8 and is dimensioned for admitting a shank 10 of the elongated bone fixation element 9 therethrough (shown in FIG. 3) and smaller than a first portion 37 of the head 11 of the bone fixation element 9 (shown in FIG. 3) for retaining the head 11 within the interior space 32 of the coupling element 2. As shown, the hole 13 is dimensioned for housing a bone fixation element head 11 having at least a partially spherical shape, thereby permitting rotational movement of the bone fixation element 9. However, the hole 13 may be of other dimensions as well, including, but not limited to, planar or convex.

Figure 10:
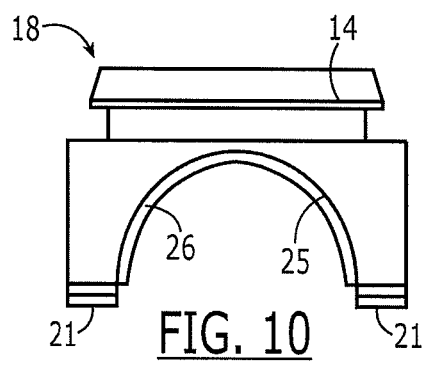
FIG. 10 is a side view of a securing element of the spinal fixation system.
Figure 11:
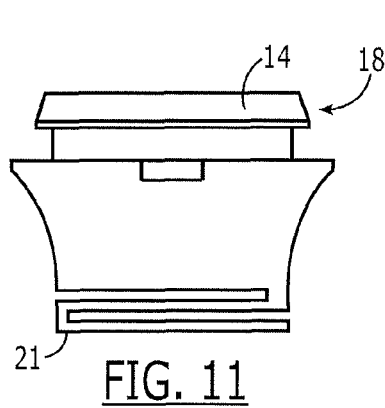
FIG. 11 is an alternate side view of a securing element of the spinal fixation system.
Figure 12:
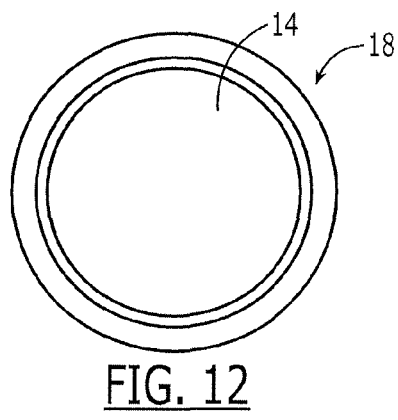
FIG. 12 is a top view of a securing element of the spinal fixation system.

FIGS. 10, 11, and 12 show varying views of a securing element of the spinal fixation system of the present invention. The securing element 18 may include an upwardly extending arm 14 dimensioned for insertion into the locking element 20. As shown, the arm 14 is substantially T-shaped; however, other shapes may be utilized. A biasing member 21 may be located on the lower portion 44 of the securing element 18, and an optional raised portion 26 may be located on the concave surface 25 of the securing element 18.

Figure 13:
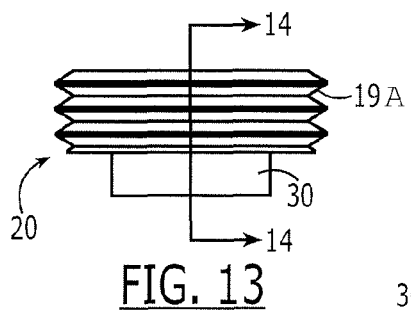
FIG. 13 is a side view of a locking element of the spinal fixation system.
Figure 14:
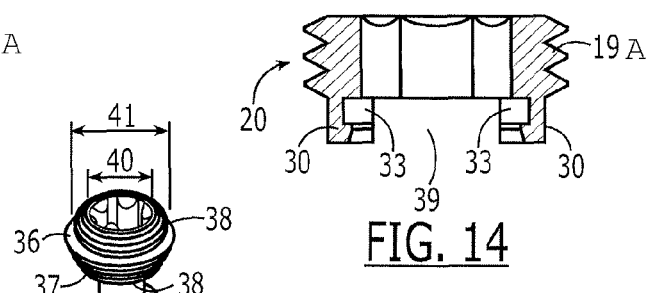
FIG. 14 is a cross-sectional view along lines 14-14 of the embodiment of FIG. 13.

FIGS. 13 and 14 show varying views of a locking element of the spinal fixation system. The locking element 20, which is an optional component of the spinal fixation system 1, may include a mating element 19A located on an external surface thereon and a downwardly extending wall 30. The wall 30 defines a locking element interior space 39 dimensioned for housing the arm 14 of the securing element 18 and may include at least one groove 33 located therein. Moreover, the wall 30 may be sized and shaped so as to prevent the arm 14 from dislodging, yet permit rotation of the arm 14 therein. In this manner, the securing element 20 is rotatingly secured to the locking element 18.

Figure 15:
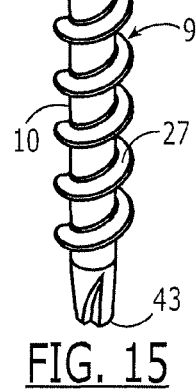
FIG. 15 is a perspective view of a bone fixation element of the spinal fixation system.

Next, FIG. 15 shows a perspective view of a bone fixation element of the spinal fixation system. The bone fixation element 9 may be a bone screw or any other type of fastener that may be utilized for insertion into a bone. The bone fixation element 9 includes a head 11, an elongated shank 10 which extends downwardly from the bone fixation element 9, and a tip 43. Bone fixation element threads 27 may be located on the shank 10 of the bone fixation element 9.

The head 11 of the bone fixation element 9 may include a first portion 36 and a second portion 37, with each portion 36 and 37 having optional teeth 38 located thereon. The first portion 36 and the second portion 37 each may be of a certain size and shape and may have certain diameters. As depicted, a first portion diameter 40 is less than a second portion diameter 41. These diameters 40 and 41 of the bone fixation element 9 may be of any size; however, the second portion diameter 41 should be greater than the diameter of the hole 13 in the coupling element 2 so as to allow the head 11 of the bone fixation element 9 to remain within the coupling element 2 while the shank 10 of the bone fixation element 9 extends through the hole 13 of the coupling element 2. The second portion 37 of the bone fixation element 9 may be semi-spherical in shape to permit rotational movement of the bone fixation element 9 within the coupling means 2 when the hole 13 is dimensioned as such, for example, when the hole 13 is substantially concave. In this manner, when the bone fixation element 9 is inserted through the hole 13 of the coupling element 2, it still may be rotated and adjusted to a desired angle prior to insertion into a bone. Although the second portion 37 of the head 11 of the bone fixation element 9 is shown having a substantially round shape, other shapes may be utilized.

Figure 16:
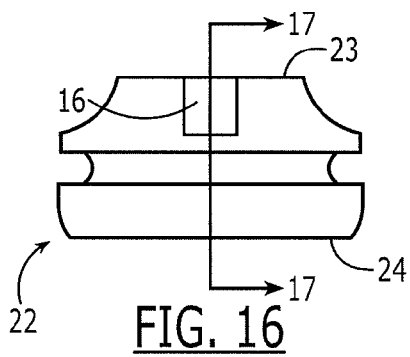
FIG. 16 is a side view of a retaining element of the spinal fixation system.
Figure 17:
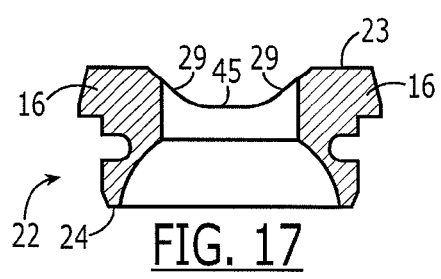
FIG. 17 is a cross-sectional view along lines 17-17 of the embodiment of FIG. 16.
Figure 18:
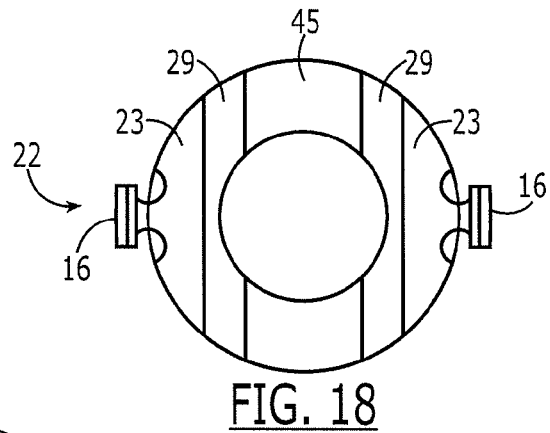
FIG. 18 is a top view of a retaining element of the spinal fixation system.

With respect to FIGS. 16, 17, and 18, varying views of a retaining element of the spinal fixation system are shown. The retaining element 22 includes a top surface 23 and a bottom surface 24. The retaining element 22 may also include at least one outwardly extending wing 16. The top surface 23 of the retaining element 22 may be concave for at least partially circumscribing the diameter 12 of the fixation rod 15 when the fixation rod 15 is admitted into the apertures 17 of the coupling element 2. Contact areas 29 are located on the retaining element 22 such that the fixation rod 15 makes contact with the contact areas 29 of the retaining element 22. The contact areas 29 may be sloped. Although a substantially concave top surface 23 is shown, the top surface 23 may also be of any other form including, but not limited to, planar or convex.

The bottom surface 24 of the retaining element 22 may be generally concave and, as shown, generally spherical, so as to accommodate at least a portion of the first portion 36 of the head 11 of the bone fixation element 9. As the retaining element 22 is driven onto the first portion 36, the pressure between the retaining element 22 and the first portion 36, and the retaining element 22 and coupling element 2, becomes greater. In this manner, limited motion between the bone fixation element 9 and the retaining element 22 is permitted. Although the bottom surface 24 of the retaining element 22 is shown having a generally spherical shape, other shapes may also be utilized.

In addition or in the alternative, the bottom surface 24 may engage the teeth 38 on the first portion 36 of the head 11. Limited motion between the bone fixation element 9 and the retaining element 22 is permitted in this manner as well.

Figure 19:
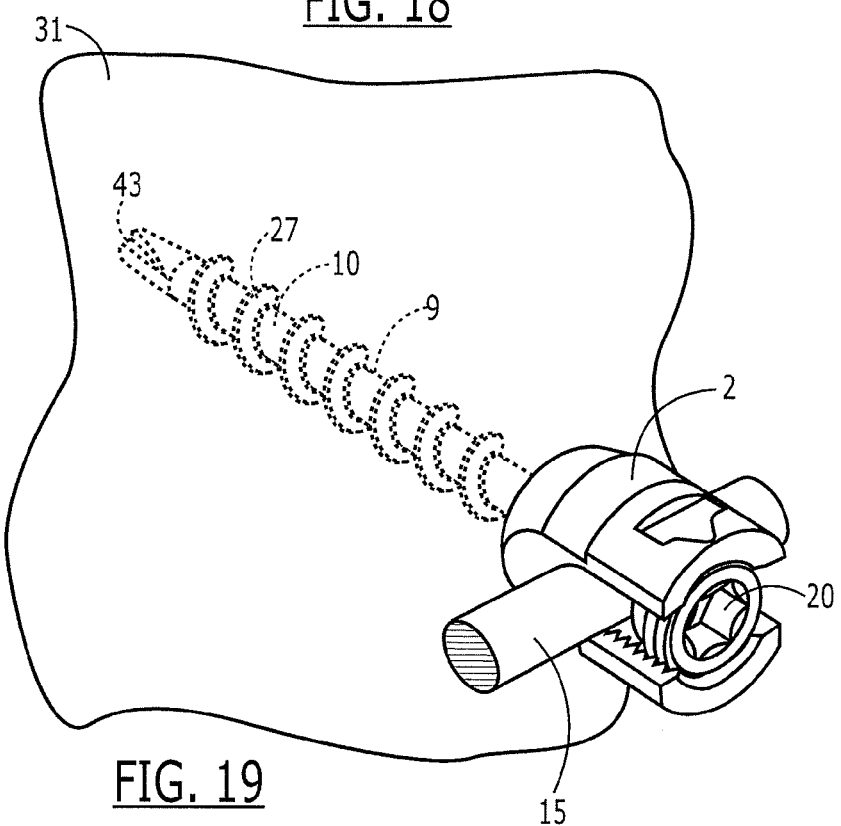
FIG. 19 is a plan view of the spinal fixation system installed in a bone in a spine.

Finally, FIG. 19 shows a plan view of the spinal fixation system installed in a bone in a spine. To use the spinal fixation system 1, a user positions the bottom end 5 of the coupling element 2 adjacent to a bone 31 of a spine. Then, the user inserts the bone fixation element 9 into the coupling element 2 such that a shank 10 is located within the interior space 32 and the tip 43 extends into the hole 13 and is adjacent to the bone 31. The user then drives the bone fixation element 9 into the bone 31 such that at least a portion of a shank 10 extends through the hole 13 and into the bone 31. The bone fixation element 9 may be driven into the bone 31 via various methods, such as, but not limited to, rotation or impact of the bone fixation element 9.

The retaining element 22 is then inserted within the coupling element 2 and positioned on the first portion 36 of the head 11 of the bone fixation element 9. The fixation rod 15 is then admitted into the apertures 17. The securing element 18 is then inserted into the coupling element 2 such that the biasing members 21 of the securing element 18 make contact with the retaining element 22. The user then rotates the locking element 20 such that the mating element 19 of the locking element 20 mates with the mating element 19 of the coupling element 2.

When the locking element 20 is tightened, a force is applied to the securing element 18. The force from the securing element 18 then translates force onto the retaining element 22. As the locking element 20 is tightened, the securing element 18 moves in a downward direction, first compressing the biasing members 21, then applying direct pressure on the fixation rod 15. The force applied on the fixation rod 15 translates force onto the contact area 29 of the retaining element 22. Thus, the head 11 of the bone fixation element 9 is locked first, then the fixation rod 15 is locked. These forces work together to compress a crimping portion 42 of the retaining element 22. Additionally, as the locking element 20 is tightened, the securing element 18 and the retaining element 22 are wedged within the coupling element 2, thereby providing greater securement.

If threads 27 are provided on the bone fixation element 9, then an additional amount of force may be required when driving the bone fixation element 9 into the bone 31. However, use of bone fixation elements 9 having threads 27 thereon provide greater retention of the spinal fixation system 1 within the bone 31.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A spinal fixation system for use in the fixation of a spine comprising:
   (i) a coupling element having a generally cylindrical wall and a pair of opposed longitudinal apertures through the wall and extending from a top end of the coupling element to an aperture bottom in spaced relation from a bottom end of the coupling element, the generally cylindrical wall defining an interior space of the coupling element dimensioned for admitting a bone fixation element thereinto, the apertures dimensioned for admitting a fixation rod diametrically through the interior space of the coupling element; and a hole through the bottom end of the coupling element dimensioned for admitting a shank of the elongated bone fixation element therethrough, the hole being smaller than a head of the bone fixation element for retaining the head within the interior space of the coupling element, the shank of the bone fixation element extending downwardly from the head of the bone fixation element, the bone fixation element head having a first portion of a first size and a second portion of a second size which is greater than the first size of the first portion, threads on exterior surfaces of the first portion being in contact with the bottom portion of the retaining element;
   (ii) a securing element having a generally cylindrical body configured to fit within the coupling element, a biasing member located on a lower portion of the securing element; and
a substantially concave surface dimensioned for at least partially circumscribing a fixation rod; and
   (iii) a retaining element having:
      a substantially concave top surface dimensioned for at least partially circumscribing a fixation rod;
      an outwardly extending wing;
      a crimping portion, wherein the crimping portion at least partially compresses when a force is exerted on the retaining element; and
      a substantially concave bottom surface dimensioned for at least partially circumscribing a head of a bone fixation element,
      wherein: the substantially concave top surface of the retaining element has a contact area, wherein the contact area is a linear increasing slope extending from a base section toward the wing and wherein the configuration of the contact area does not match the outer surface contour of the fixation rod.

2. A spinal fixation system for use in fixation of a spine comprising:
   (i) a coupling element, the coupling element having:
      a generally cylindrical wall and a pair of opposed longitudinal apertures through the wall and extending from a top end of the coupling element to an aperture bottom in spaced relation from a bottom end of the coupling element, the generally cylindrical wall defining an interior space of the coupling element dimensioned for admitting a bone fixation element thereinto, the apertures dimensioned for admitting a fixation rod diametrically through the interior space of the coupling element; and
      a hole through the bottom end of the coupling element dimensioned for admitting a shank of the elongated bone fixation element therethrough, the hole being smaller than a head of the bone fixation element for retaining the head within the interior space of the coupling element, the shank of the bone fixation element extending downwardly from the head of the bone fixation element;
   (ii) a retaining element having a generally cylindrical body and dimensioned for insertion into the interior space of the coupling element atop the head of the bone fixation element, the retaining element configured to retain the fixation rod within the interior space of the coupling element, and having:
      a substantially concave top surface dimensioned for at least partially circumscribing the fixation rod;
      a pair of outwardly extending wings which extend radially outward from the generally cylindrical body;
      a compressible portion, wherein the compressible portion is configured to at least partially compresses when a force is exerted on the body of the retaining element; and
      a bottom portion configured to house at least a portion of the bone fixation element head, and to permit rotational movement of the bone fixation element within the retaining element, the bone fixation element head having a first portion of a first size and a second portion of a second size which is greater than the first size of the first portion, threads on exterior surfaces of the first portion being in contact with the bottom portion of the retaining element;
   (iii) a securing element dimensioned for insertion into the coupling element interior space atop the fixation rod, the securing element having:
      a compressible biasing member located on a lower portion of the securing element, the compressible biasing member configured for compression against the retaining element and in contact with the pair of outwardly extending wings of the retaining member; and
      a substantially concave bottom surface dimensioned for at least partially circumscribing the fixation rod; and
   (iv) locking element engaged with the coupling element at the top end of the coupling element and retaining the fixation rod within the interior space of the coupling element,
      and wherein: the substantially concave top surface of the retaining element has a contact area, wherein the contact area is a linear increasing slope extending from a base section toward the wing and wherein the configuration of the contact area does not match the outer surface contour of the fixation rod.

3. The bone fixation system of claim 2 wherein the bone fixation element head having a first portion of a first size and a second portion of a second size which is greater than the first size of the first portion, threads on exterior surfaces of the first portion being in contact with the bottom portion of the retaining element, and threads on exterior surfaces of the second portion in contact with an interior surface of the coupling element proximate to the hole in the coupling element and not in contact with the retaining element.

4. The bone fixation system of claim 3 wherein the threads on the exterior surfaces of the first portion of the bone fixation element head are in contact with the retaining element proximate to the compressible portion of the retaining element.

5. The bone fixation system of claim 3 wherein the retaining element does not contact the second portion of the bone fixation element head.

6. The bone fixation system of claim 2 further comprising a washer which substantially encircles the retaining element at a location between the pair of outwardly extending wings of the retaining element and a bottom portion of the retaining element, the washer also substantially encircling the first portion of the bone fixation element head.

7. A spinal fixation system comprising:
a bone fixation element having a shank adapted for insertion into a bone, the bone fixation element having a bone fixation element head at one end of the shank, the bone fixation element head having a first portion of a first size and a second portion which extends from and forms a distal end of the bone fixation element;
a coupling element having a generally cylindrical body formed by a generally cylindrical wall and a cavity within the generally cylindrical wall, a first opening at a first end of the body and a second opening at a second end of the body, the bone fixation element shank extending axially through the second opening, and the first portion of the bone fixation element head in contact with an interior of the wall of the coupling element proximate to the second opening;
the second portion of the bone fixation element head extending from the first portion and forming a distal end of the bone fixation element and located within the cavity of the coupling element and not in contact with the interior of the wall of the coupling element proximate to the second opening;
a retainer element located in the cavity of the coupling element and in contact with the second portion of the bone fixation element head and in contact with a fixation rod which passes transversely through the cylindrical wall of the coupling element;
a securing element located in the cavity of the coupling element generally opposed to and in contact with the retainer element and in contact with the fixation rod, and
a locking element engaged with the coupling element and located in the first opening of the coupling element;
wherein the retainer element further comprises laterally extending wings in contact with the securing element; and
wherein the securing element further comprises compressible biasing members in contact with the retainer element.

8. The spinal fixation system of claim 7 wherein the compressible biasing members of the securing element are in contact with the laterally extending wings of the securing element.

\* \* \* \* \*